United States Patent [19]
Lindenmeyer et al.

[11] Patent Number: 5,599,283
[45] Date of Patent: Feb. 4, 1997

[54] ORTHOPEDIC APPLIANCE RETAINER

[76] Inventors: Carl W. Lindenmeyer, 36 W. 270 Crane Rd., St. Charles, Ill. 60175; Claire L. Watgen, 200 N. Island Ave. #217, Batavia, Ill. 60510

[21] Appl. No.: 428,347

[22] Filed: Apr. 25, 1995

[51] Int. Cl.$^6$ .................................................. A61F 5/00
[52] U.S. Cl. ................... 602/5; 602/20; 602/23
[58] Field of Search ....................... 602/62, 63, 64, 602/65, 77; 128/878, 882

[56] References Cited

U.S. PATENT DOCUMENTS

| | | | |
|---|---|---|---|
| 680,477 | 8/1901 | Drosness | 602/64 |
| 692,503 | 2/1902 | Bottomley | 602/63 X |
| 2,082,599 | 11/1933 | Sawyer | 602/62 X |
| 3,535,718 | 10/1970 | Murcott. | |
| 3,892,239 | 7/1975 | Masso Remiro | 602/63 X |
| 4,027,666 | 6/1977 | Marx. | |
| 4,098,268 | 7/1978 | Scott. | |
| 4,414,969 | 11/1983 | Heyman. | |
| 4,459,980 | 7/1984 | Perser et al.. | |
| 4,492,227 | 1/1985 | Senn et al. | 602/63 |
| 4,530,350 | 7/1985 | Brown et al.. | |
| 4,693,239 | 10/1987 | Clover, Jr.. | |
| 4,702,233 | 10/1987 | Omicioli | 128/DIG. 23 |
| 4,864,698 | 10/1989 | Brame. | |
| 5,015,251 | 5/1991 | Cherubini. | |
| 5,214,874 | 6/1993 | Faulkner. | |
| 5,309,926 | 5/1994 | Mayton | 128/869 |
| 5,338,290 | 8/1994 | Aboud | 602/62 X |
| 5,352,209 | 10/1994 | Bird et al. | 604/179 |

*Primary Examiner*—Richard J. Apley
*Assistant Examiner*—David R. Risley
*Attorney, Agent, or Firm*—Emrich & Dithmar

[57] ABSTRACT

A retainer disposed about a body part such as a limb engages in orthopedic appliance such as a cast or a knee or elbow brace and maintains the orthopedic appliance securely in fixed position on the body part. In the case of a leg or arm brace or cast, the retainer is disposed about and engages a distal portion of the user's leg or arm for preventing the orthopedic appliance from sliding down the limb. The band-like, flexible retainer includes an inner lining engaging the limb and having a high coefficient of friction with skin to securely maintain the retainer in position, an outer layer including a fastening arrangement such as hook and loop fiber portions, and an intermediate layer having sufficient thickness to engage an end of the orthopedic appliance and provide support for the appliance. The retainer prevents the orthopedic appliance from sliding along the limb such as under the influence of gravity and maintains the appliance in fixed position on the limb. The retainer's inner layer is comprised of or has a coating of silicone rubber and may be in the form of a smooth, continuous or apertured layer, or may be textured or include spaced projections, to allow for air circulation on the user's skin.

9 Claims, 2 Drawing Sheets

ORTHOPEDIC APPLIANCE RETAINER

FIELD OF THE INVENTION

This invention relates generally to orthopedic appliances such as braces and casts and is particularly directed to apparatus for securely maintaining an orthopedic appliance in fixed position on a body part such as a limb.

BACKGROUND OF THE INVENTION

Injury or disease frequently cause a weakening of a patient's limb such as an arm or leg requiring additional support such as in the form of a brace. In some cases, immobilization of the limb is required and a rigid cast is used to encase the limb. After swelling of the tissue surrounding the injury subsides, the cast frequently becomes rather loose fitting and is subject to movement from its intended position on the limb. This frequently causes discomfort for the user and, in some cases, may retard or impede the healing process. This same situation is frequently encountered in orthopedic braces which may become increasingly loose fitting once the healing process begins. In addition, orthopedic braces generally are available in only a limited number of sizes, i.e., small, medium and large, and are not generally custom-fitted to the user. This also leads to a loose fitting appliance which not only fails to provide its intended benefit to the user, but may also aggravate the injury or cause additional damage.

The present invention addresses the aforementioned problems of the prior art by providing a retainer for an orthopedic appliance which maintains the appliance securely in fixed position on the body part. The retainer is easily installed and removed and its position on the body part may be easily and quickly adjusted for the comfort and recovery of the wearer.

OBJECTS AND SUMMARY OF THE INVENTION

Accordingly, it is an object of the present invention to securely maintain an orthopedic appliance such as a brace or cast in fixed position on a body part such as a limb.

It is another object of the present invention to provide a retainer for a conventional orthopedic brace or cast which maintains the brace or cast in fixed position on a body part such as a leg or arm.

Yet another object of the present invention is to provide a band-like retainer which is attached in a fixed manner to a body part such as a limb, yet is easily installed and removed, for engaging and maintaining an orthopedic appliance disposed on the body part in fixed position thereon.

This invention contemplates apparatus for maintaining an orthopedic appliance securely in fixed position on a person's limb or other body part, the apparatus comprising: an outer flexible member of sufficient length to encircle the limb or other body part and including fastening means for securely attaching the outer member to the limb or other body part about the periphery thereof; an inner flexible member disposed in a tight fitting manner about the person's limb or other body part and engaging the person's skin, the inner member having an inner surface with a high coefficient of friction with human skin to prevent movement of the inner member on the limb or other body part; and an intermediate flexible member disposed between and attached to the outer and inner members for engaging an end of and supporting the orthopedic appliance and preventing movement of the orthopedic appliance on the limb or body part.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE PREFERRED EMBODIMENTS

Figure 1:
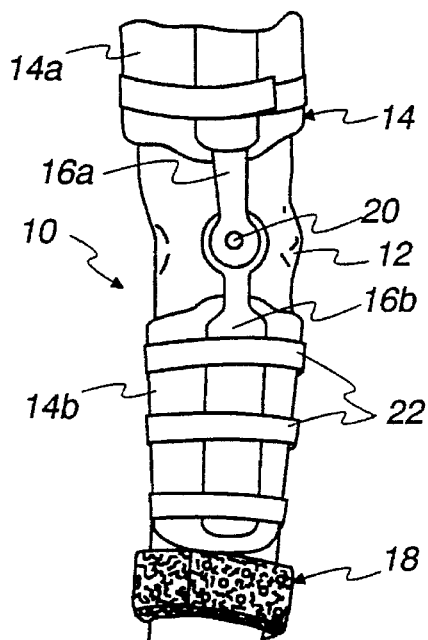
FIG. 1 is a side elevation view of a hinged elbow brace in position on a user's arm illustrating the orthopedic appliance retainer of the present invention engaging and maintaining the elbow brace in fixed position on the arm.

Referring to FIG. 1, there is shown a side elevation view of an arm brace 14 attached to a user's arm 10 adjacent the user's elbow 12. In the following discussion, the terms "user", "wearer" and "person" are used interchangeably. Arm brace 14 is conventional in design and operation and includes an upper brace member 14a and a lower brace member 14b. Arm brace 14 further typically includes upper and lower rigid reinforcing members 16a and 16b movably coupled together by means of a pivot pin 20. A similar combination of upper and lower reinforcing members is disposed on the inside portion of the arm brace 14, although these components are not shown in the figure for simplicity. Straps 22 disposed about the upper and lower brace members 14a, 14b maintain the brace 14 in position on the user's arm 10.

An orthopedic appliance retainer 18 in accordance with the present invention is disposed adjacent to and in contact with a lower end of the arm brace 14 for maintaining the arm brace securely in fixed position on the user's arm 10. Arm brace 14 is typically not custom fitted to the user's arm and tends to work itself somewhat loose from the arm with continued use. Moreover, the typical arm brace is available in a limited number of sizes and is invariably loose fitting for a person with small limbs. Retainer 18 prevents the arm brace 14 from sliding down the user's arm and maintains the hinge of the brace in alignment with the user's elbow 12. In this manner, the arm brace 14 allows for flexure of the user's arm without impeding and causing discomfort, and possibly injury, to the brace wearer. The orthopedic appliance retainer 18 is in the general form of a bracelet, having an outer layer which is adapted for securely maintaining the retainer in position around the limb, an inner layer which is characterized as having a high coefficient of friction with human skin to insure fixed positioning of the retainer on the limb, and an intermediate layer which provides sufficient retainer thickness for engaging and supporting the brace and functions as a cushion for the brace for increased comfort of the brace wearer.

Figure 2:
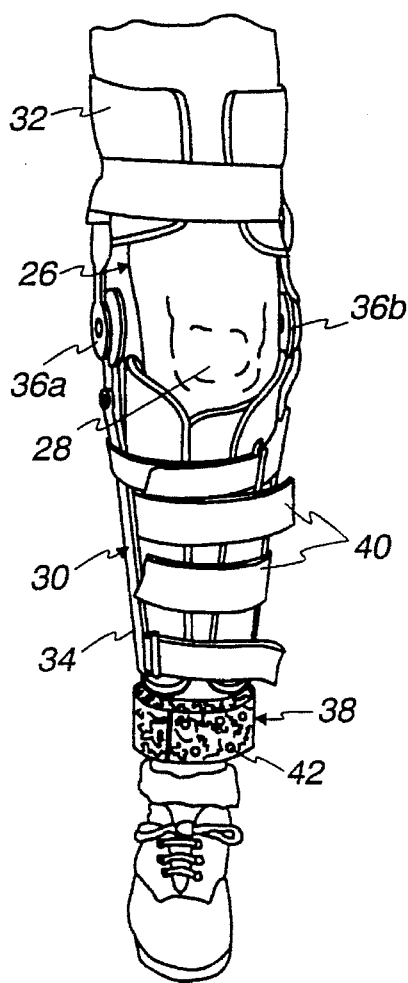
FIG. 2 is a front elevation view of a hinged knee brace in position on a user's leg illustrating the orthopedic appliance retainer of the present invention engaging and maintaining the brace in fixed position on the leg.

Referring to FIG. 2, there is shown a front elevation view of a leg 26 on which is disposed a leg brace 30 maintained securely in position by means of an orthopedic appliance retainer 38 in accordance with the present invention. As in the case of the arm brace described above, leg brace 30 includes an upper brace member 32 and a lower brace member 34 pivotally coupled together by means of first and second hinges 36a and 36b. Hinges 36a and 36b allow for flexure of the leg 26 at the knee 28. A plurality of straps 40 coupled to and disposed about the leg brace 30 maintain the leg brace wrapped around leg 26. By engaging a lower end portion of leg brace 30, retainer 38 maintains the leg brace in fixed position on the user's leg 26 and prevents the brace from sliding down the leg. In the embodiments of the orthopedic appliance retainer shown in FIGS. 1 and 2, the outer layer of the retainer is comprised of a hook and loop fabric combination for positioning the retainer in a tight fitting manner about the user's limb. In addition, the retainers shown in FIGS. 1 and 2 are each provided with a plurality of spaced apertures 42 to allow for air circulation about the user's limb in the vicinity of the retainer 38.

Figure 3:
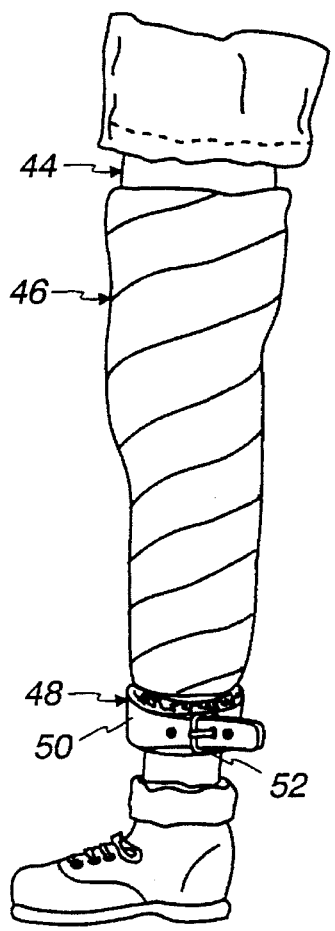
FIG. 3 is a side elevation view of a cast in position on a user's leg illustrating the orthopedic appliance retainer of the present invention engaging and maintaining the cast in fixed position on the leg.

Referring to FIG. 3, there is shown a side elevation view of another embodiment of a orthopedic appliance retainer 48 for use in maintaining a cast 46 in position on a user's leg 44. Following a leg injury and after a cast 46 as shown in FIG. 3 has been applied to the injured leg, swelling associated with the injury subsides. With the swelling reduced or perhaps eliminated, cast 46 becomes loose fitting on leg 44 allowing the cast to slide up and down on the user's leg. This not only causes discomfort to the cast wearer, but also results in the cast not maintaining the leg in a fixed position as intended. In order to prevent downward sliding of cast 46 on leg 44, an orthopedic appliance retainer 48 in accordance with the present invention is affixed to the leg so as to engage a lower end portion of the cast and maintain the cast in fixed position on the leg. In the embodiment shown in FIG. 3, retainer 52 includes a strap 50 and buckle 52 combination for maintaining the retainer tightly wrapped around the user's leg.

Figure 4:
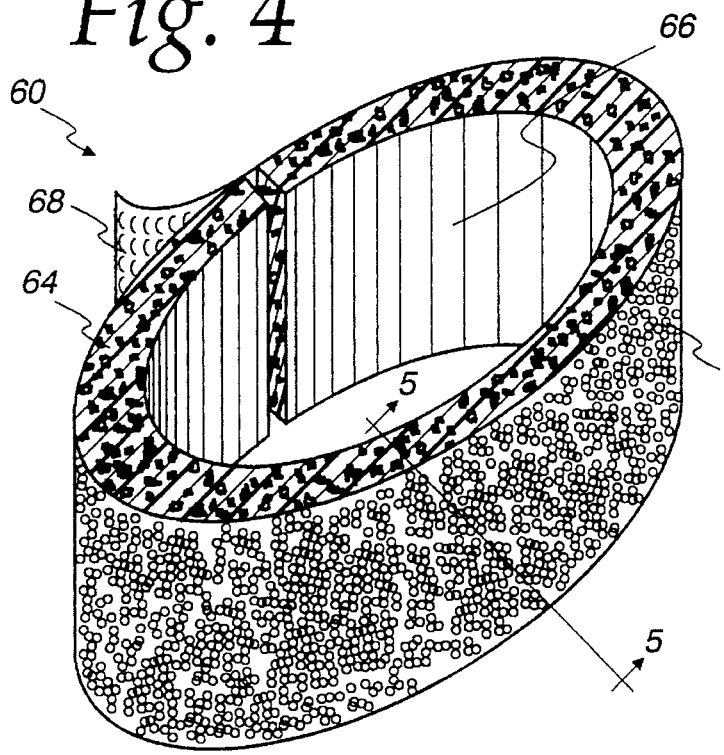
FIG. 4 is a perspective view of an orthopedic appliance retainer in accordance with the present invention.
Figure 5:
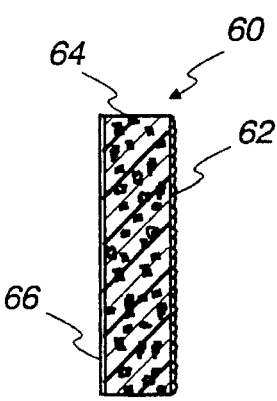
FIG. 5 is a sectional view of the orthopedic appliance retainer of FIG. 4 taken along site line 5—5 therein.

Referring to FIG. 4, there is shown a perspective view of an orthopedic appliance retainer 60 in accordance with one embodiment of the present invention. Retainer 60 includes an outer layer 62, an inner layer 66, and an intermediate layer 64 disposed between and coupled to the outer and inner layers. FIG. 5 is a sectional view of the orthopedic appliance retainer 60 shown in FIG. 4 taken along site line 5—5 therein. Outer layer 62 in the embodiment shown in FIG. 4 is in the form of a hook and loop strap such as of the Velcro type. Thus, the outer surface of outer layer 62 is provided with a hook (or loop) material, while the end portion of the inner surface 68 of the outer layer is provided with a complementary loop (or hook) material. This allows the retainer 60 to be secured about a limb (not shown in the figure for simplicity) in a tight fitting manner. Other coupling arrangements for securely maintaining the orthopedic appliance retainer in position on a body part are described below. Inner layer 66 is preferably comprised of a material having a high coefficient of friction with human skin. An example of such a material is silicone conformal coating No. 3-1753 sold by Dow Corning of South Saginaw Road, Midland, Mich. 48686. The high frictional resistance between the wearer's skin and the retainer's inner layer 66 may be provided by other equivalent coating layers for securely maintaining the retainer in position. Intermediate layer 64 has sufficient thickness to engage and support the orthopedic appliance and is affixed to the outer layer 62 by conventional adhesive means such as a pressure sensitive adhesive backing or by stitching. Intermediate layer 64 is preferably comprised of a resilient, compressible material so as to also serve as a cushion for enhanced comfort for the user. An example of the composition of the intermediate layer 64 in one embodiment is poron urethane No. 4708-01-20375-1614 available from Rogers Corp., Poron Materials Division, Woodstock Road, Box 158, East Woodstock, Conn. 06244. The intermediate layer 64 provides the orthopedic appliance retainer 60 with sufficient thickness and width for engaging and supporting the orthopedic appliance with which it is in contact.

Figure 6:
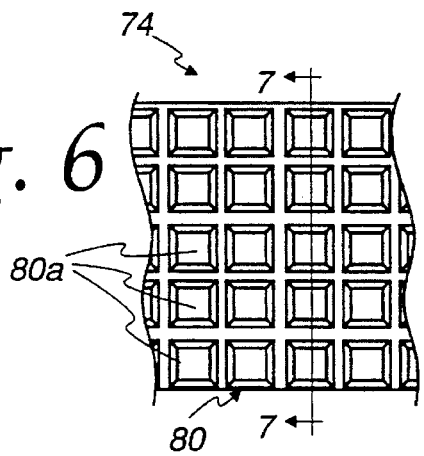
FIG. 6 is a plan view of a portion of the inner layer of another embodiment of an orthopedic appliance retainer in accordance with the present invention.
Figure 7:
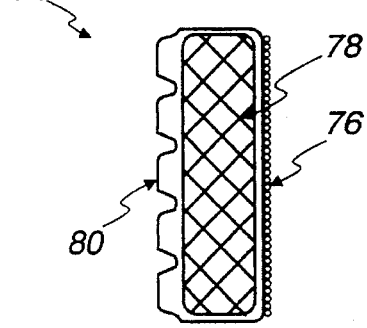
FIG. 7 is a sectional view of the orthopedic appliance retainer of FIG. 6 taken along site line 7—7 therein.

Referring to FIG. 6, there is shown a plan view of a portion of another embodiment of an orthopedic appliance retainer 74 in accordance with the present invention. A sectional view of the orthopedic appliance retainer 74 of FIG. 6 taken along site line 7—7 therein is shown in FIG. 7. As in the previously described embodiment, orthopedic appliance retainer 74 includes an outer layer 76, an inner layer 80, and an intermediate layer 78 disposed between the outer and inner layers. Outer layer 76 preferably includes a material having a hook an loop coupling arrangement as previously described for securely positioning the orthopedic appliance retainer 74 on a body part. Also as in the previously described embodiment, intermediate layer 78 is preferably comprised of a soft foam or elastomer material for the comfort of the wearer and has sufficient strength and thickness to engage and support an orthopedic appliance. Inner layer 80 is preferably comprised of silicone rubber or other elastomer having a high coefficient or friction with human skin and may be cast around and fully enclose the foam intermediate layer 78. In the embodiment shown in FIGS. 6 and 7, the inner layer 80 is provided with a plurality of spaced projections 80a defining channels which allow air to circulate between the retainer and the wearer's skin for increased comfort.

Figure 8:
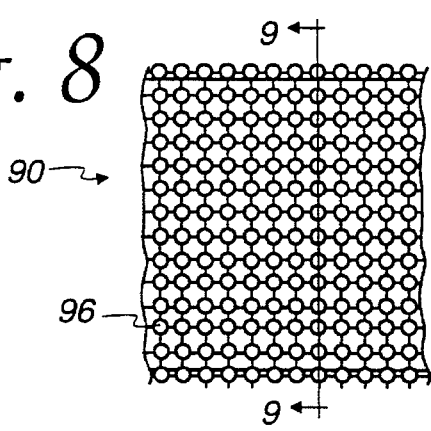
FIG. 8 is a plan view of a portion of the inner layer of yet another embodiment of an orthopedic appliance retainer in accordance with the present invention.
Figure 9:
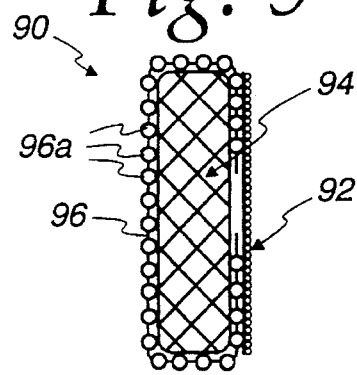
FIG. 9 is a sectional view of the orthopedic appliance retainer of FIG. 8 taken along site line 9—9 therein.

Referring to FIG. 8, there is shown yet another embodiment of an orthopedic appliance retainer 90 in accordance with the present invention. A sectional view of the orthopedic appliance retainer 90 of FIG. 8 taken along site line 9—9 therein is shown in FIG. 9. As in the previously described embodiments, retainer 90 includes an outer layer 92 comprised of a material having a hook and loop coupling arrangement. The retainer's intermediate layer 94 is preferably comprised of a compressible, resilient material which serves as a cushion for the wearer in engaging and supporting an orthopedic appliance in contact with the retainer. Attached to the intermediate layer 94 is an inner mesh layer 96 comprised of a large number of connected elastomer beads 96a which engage the wearer's skin. The inner layer 96 comprised of the elastomer beads 96a is coated such as by spraying with a silicone conformal coating as previously described to provide high frictional engagement with the wearer's skin. The spaced arrangement of the elastomer beads 96a allows air to flow between the retainer and the wearer's skin. The inner mesh layer 96 may be attached to the foam intermediate layer 94 by conventional means such as a hot melt adhesive or an epoxy cement. The same coupling arrangement may be used to attach the outer layer 92 to that portion of the inner layer 96 disposed between the outer layer and intermediate layer 94 as shown in FIG. 9.

There is thus been shown an orthopedic appliance retainer in the general form of a band or a bracelet which is adapted for engaging and supporting an orthopedic appliance such as a cast or a knee or elbow hinged brace and maintaining the appliance in fixed position on a body part, such as a limb. The retainer is comprised of a laminated structure including an outer layer, an inner layer, and an intermediate layer disposed between the outer and inner layers. The outer layer functions as a strap or coupling member for securing the retainer around a body part such as an arm or leg in a tight fitting manner. The outer layer may include a conventional hook and loop fastener of the Velcro type or may include virtually any type of belt or strap structure including conventional fastener means such as a buckle or retaining clip. The intermediate layer is preferably comprised of a compressible, resilient material which engages and provides support for the orthopedic appliance and also functions as a cushion. The inner layer is preferably comprised of or coated with a silicone material having a high coefficient of friction with human skin for securely maintaining the retainer in position on the body part. The retainer's inner layer may have either a smooth surface comforming to generally the outer surface of the body part, or may include a plurality of raised, spaced projections to allow for air circulation between the retainer and body part for increased comfort. The orthopedic appliance retainer is easily attached to and removed from the body part and is easily repositioned on the body part. The retainer is also easily cut to size in accordance with the dimensions of the body part with which it is used and is easily cleaned and may be adorned with decorative patterns for improved aesthetics.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:
1. Apparatus comprising:
   an orthopedic, appliance attached to a person's limb or other body part;
   an outer flexible, inelastic member of sufficient length to encircle the limb or other body part and including fastening means for securely attaching said outer member to the limb or other body part about the periphery thereof;
   an inner flexible member disposed in a tight fitting manner about the person's limb or other body part and engaging the person's skin, said inner member including an inner surface material having a high coefficient of friction with human skin to prevent movement of the inner member on the limb or other body part; and
   an intermediate flexible member disposed between and attached to said outer and inner members, wherein said intermediate flexible member is of sufficient thickness and width for engaging an end of and supporting the orthopedic appliance and preventing movement of the orthopedic appliance on the limb or body part.

2. The apparatus of claim 1 wherein said fastening means includes a hook and loop fabric coupling arrangement.

3. The apparatus of claim 1 wherein said fastening means includes a strap and buckle combination.

4. The apparatus of claim 1 wherein said inner member includes silicone rubber conformal coating for frictionally engaging the person's skin and securely maintaining the apparatus securely in position thereon in a fixed manner.

5. The apparatus of claim 4 wherein said inner member further includes a plurality of spaced projections engaging the person's skin and defining a plurality of channels for allowing air circulation between the apparatus and the person's skin.

6. The apparatus of claim 1 wherein said inner member includes a mesh structure comprised of silicone rubber and having a plurality of spaced beads engaging the person's skin and defining a plurality of channels for allowing air circulation between the apparatus and the person's skin.

7. The apparatus of claim 1 wherein said inner member includes a mesh structure having a coating of silicone rubber and including a plurality of spaced beads engaging the person's skin and defining a plurality of channels for allowing air circulation between the apparatus and the person's skin.

8. The apparatus of claim 1 wherein said intermediate member is comprised of a compressible, resilient material and serves as a cushion for the orthopedic appliance.

9. The apparatus of claim 8 wherein said compressible, resilient material is polyurethane foam.

\* \* \* \* \*